United States Patent [19]

Boston

[11] Patent Number: 4,460,511

[45] Date of Patent: Jul. 17, 1984

[54] PRODUCTION OF ANTIMONY ORGANOPHOSPHORODITHIOATES

[75] Inventor: Ernest B. Boston, Phillips, Tex.

[73] Assignee: Phillips Petroleum Company, Bartlesville, Okla.

[21] Appl. No.: 416,774

[22] Filed: Sep. 10, 1982

[51] Int. Cl.³ .............................................. C07F 9/90
[52] U.S. Cl. .................................................... 260/446
[58] Field of Search ........................................ 260/446

[56] References Cited

U.S. PATENT DOCUMENTS 4,394,323  7/1983  Lowery et al. ...................... 260/446
4,394,324  7/1983  Mark et al. .......................... 260/446

Primary Examiner—Helen M. S. Sneed

[57] ABSTRACT

The stability of antimony salts of hydrocarbylphosphorodithioic acids is improved by adding thereto certain alcohols.

6 Claims, No Drawings

PRODUCTION OF ANTIMONY ORGANOPHOSPHORODITHIOATES

BACKGROUND

In the catalytic cracking of hydrocarbons, meta contaminants are passivated by adding to the catalysts certain antimony compounds. Until now, one widely used group of compounds has been difficult to store and handle, due to haze formation and phase separation therein.

INVENTION

It has been discovered that antimony salts of dihydrocarbylphosphorodithioic acids can be stabilized against haze formation and phase separation by the use of one or more alcohol additives.

In one embodiment, antimony tris(di-n-propyl phosphorodithioate), which had decomposed to form a hazy liquid comprising immiscible phases, was clarified by the addition thereto of isopropyl alcohol.

OBJECTS OF THE INVENTION

It is an object of the invention to stabilize antimony organophosphorodithioates.

It is a further object of the invention to minimize the handling and storage requirements of certain antimony salts.

It is another object of the invention to prepare antimony-containing passivators with minimal production of decomposition products.

It is yet another object of the invention to minimize the problems associated with the transfer and use of antimony passivating agents.

It is still another object to facilitate the production and quality control of antimony organophosphorodithioate manufacture by preventing the haze formation and phase separation problems associated therewith.

ADVANTAGES

Antimony hydrocarbylphosphorodithioates containing stabilizing additives of this invention have several advantages over salts which do not. The minimization of haze and phase separation means that storage tanks, reaction vessels, and transfer equipment, e.g., pumps and nozzles, stay clean longer because the clogging, clouding, and dirty-appearance problems normally associated with the salts are significantly reduced.

While the exact nature of the substance which causes the haziness is not known, it is speculated that haziness is greater when "old" hydrocarbylphosphorodithioic acids are used. It is known that the insoluble liquid phase which separates to the bottom of the salt containers is highly acidic. It is believed to be hydrolysis products of the acid and probably contains organic phosphates, thiophosphates and/or their acid analogs.

DESCRIPTION OF THE INVENTION

The antimony salts used in accordance with the invention conform to the general formula

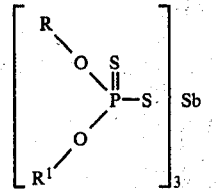

wherein R and R' can be the same or different and are hydrocarbyl radicals containing from 1 to 18 carbon atoms.

The R and R' moieties are derived from hydroxyl components such as mono-, and polyhydroxy-substituted hydrocarbons. Preferably, R and R' are derived from monohydroxy-substituted compounds containing 1 to 12 carbon atoms. Useful compounds include aromatic, cycloaliphatic, aliphatic, and branched-chain phenols and alcohols. Phenols, cyclohexanols, n-decanol, n-propanol, and isopropanol are useful.

The antimony salts can be called "antimony dihydrocarbylphosphorodithioates", "antimony tris(O,O-dihydrocarbyl)phosphorodithioates", and "antimony dihydrocarbyldithiophosphates".

The antimony hydrocarbylphosphorodithioate salts of this invention are produced via the reaction of hydrocarbylphosphorodithioic acids or their chemical equivalents with antimony compounds. Chemical equivalents for the acids include their salts with alkali metal, such as sodium and potassium.

The hydrocarbylphosphorodithioic acid reactant can be produced by a variety of methods. One method for producing the acid intermediate is the reaction of an alcohol with a phosphorus sulfide. When the intermediate is synthesized from a monoalcohol and disphosphorus pentasulfide, for example, the reaction conforms to the following equation:

$$4ROH + P_2S_5 \rightarrow 2(RO)_2PSSH + H_2S$$

Preferably, a molar excess of the alcohol reactant is used.

Use of $P_2S_5$ that has been purified by distillation is preferred because antimony compounds made therefrom are more stable against thermal decomposition.

The hydrocarbylphosphorodithioic acid is reacted with one or more of a large group of antimony-containing compounds. Suitable antimony compounds conform to the general formula

$$Sb_mX_n$$

wherein X is —O, —OH, —OOCR", —Cl, —Br, or —F; R" is an organic radical containing 1 to 12 carbon atoms; and m and n are independent and represent numbers from 1 to 5. The oxides, hydroxides, acetates, and chlorides of antimony are among the useful compounds. Preferred compounds include the oxides and hydroxides of antimony.

The antimony compound can be added to the acid intermediate alone or in admixture with an inert hydrocarbon carrier.

Normally, the acid is added to the compound, preferably suspended in a hydrocarbon carrier, at a controlled rate, so that the temperature, which increases because of the exothermic reaction, is not permitted to exceed about 50° C.

One method of making the antimony salts used herein is disclosed in U.S. Pat. No. 3,471,540, the disclosure of which is incorporated herein by reference.

Another method for producing the anitmony salts can be described as follows:

About 97% of the total quantity of antimony trioxide in kerosene is added to the reactor. 100% of the total organophosphorodithioic acid reactant is added thereto while maintaining the reactor at temperatures of 43° C. or below. The resultant solution is green.

Increments of antimony oxide containing about 0.5% of the stoichiometric quantity are added to the reactor at half-hour intervals. As the increments are added, the color of the solution changes from green to yellow, indicating the progress of the neutralization. When a light yellow color occurs and is maintained, the reaction is complete. Water of condensation is removed from the reactor. The product is then cooled and filtered using conventional filters, such as Cuno or Sparkler filters.

Plant batches of antimony organophosphorodithioates often form a haze which interferes with production and quality control. After standing for a period of time, on the order of a few days, this haze settles to the bottom of the containers as a distinct liquid phase. If it is permitted to remain in the containers, the immiscible portion can cause clogging when the salt is pumped into reaction vessels, e.g., catalytic crackers, for passivation purposes.

The antimony salts produced in accordance with the invention can be employed as passivation agents in catalytic cracking systems. Systems in which they are operable include those disclosed in U.S. Pat. Nos. 4,031,002 and 4,166,806. The disclosures of these patents are incorporated herein by reference.

THE ALCOHOL ADDITIVES

The alcohol additives used herein are hydroxyl-substituted alkanes, i.e., alkanols. Generally, they conform to the structural formula

R—OH wherein R contains at least one aliphatic, cycloaliphatic, or branched-chain group. R is preferably a paraffinic moiety containing from 1 to about 12, most preferably from 3 to 6, carbon atoms.

Typical alcohols of the invention include: ethanol, isopropanol, tert-butanol, n-butanol, amyl alcohol, heptanol-1, cyclohexanol, o-methyl cyclohexanol, hexanol-2, and octanol-3. Isopropanol and n-butanol are preferred with n-butanol highly preferred. Mixtures of alcohols can be employed.

The alcohol additives of the invention are used in quantities which stabilize the solution, i.e., which assure the miscibility of any compounds present, such as byproducts or decomposition products with the salt or the salt/carrier solution. Typical quantities of alcohol added will lie between about 0.2 and about 3.0 wt. %, with about 0.5-2 wt. % preferred. These percentages are based on the weight of the salt solution.

EXAMPLES

Example 1

Liquid antimony tris(di-n-propylphosphorodithioate) (75 wt. % in kerosene) was produced by reaction of $Sb_2O_3$ and di-isopropylphosphorodithioic acid as disclosed on p. 4, 1. 4–15 this application. After two days a noticeable haze had formed.

To 50 g samples of the above antimony product solution alcohol was added and mixed by shaking in 100 ml vials. Results are given in the table.

TABLE

| Alcohol | Conc. of Alcohol (wt %) | Results |
|---|---|---|
| isopropyl | 1 | Less hazy solution |
| isopropyl | 2 | clear solution within 10 min |
| n-butyl | 1 | less hazy solution |
| n-butyl | 2 | clear solution within 5 min |
| ethyl | 2 | clear solution within 5 min |
| b-butyl | 2 | clear solution within 5 min |
| n-amyl | 2 | clear solution within 5 min |
| cyclohexyl | 2 | clear solution within 5 min |
| n-heptyl | 2 | clear solution within 5 min |

The clear solution remained clear after standing as long as six months.

Example 2 (800 gal reactor-Large Scale Test)

A 600 gal batch of antimony tris(di-n-propylphosphodithioate (75% in kerosene) was prepared in an 800 gal reactor as disclosed on p. 4, 1. 4–15 this application.

After the product was filtered through a 1 micron filter, a haze remained in the product. Addition of 130 lb n-butanol (2.2 wt. %) and mixing in a roll tank dissolved the hazy material producing a clear stable product.

Reasonable variations can be made in the invention without departing from the scope thereof.

I claim:

1. A composition comprising antimony tris(di-n-propylphosphodithioate) and a stabilizing amount of at least one alcohol selected from the group consisting of isopropyl alcohol, n-butyl alcohol, ethyl alcohol, t-butyl alcohol, n-amyl alcohol and cyclohexyl alcohol, and n-heptyl alcohol.

2. A composition of claim 1 wherein the alcohol is isopropyl alcohol.

3. A process for stabilizing compositions containing one or more antimony organophosphorodithioates against haze formations and phase separation comprising adding thereto one or more alcohols.

4. The process of claim 3 wherein the alcohol used conforms to the general formula

R—OH wherein R contains at least one aliphatic, cycloaliphatic, or branched chain group.

5. The process of claim 3 wherein the alcohol is isopropanol.

6. The process of claim 3 wherein the alcohol is n-butanol.

* * * * *